(12) United States Patent
Umezaki et al.

(10) Patent No.: US 11,000,659 B2
(45) Date of Patent: May 11, 2021

(54) TRACHEOTOMY TUBE HAVING FREELY OPENABLE/CLOSABLE LATERAL HOLE

(71) Applicants: Toshiro Umezaki, Fukuoka (JP); KOKEN CO., LTD., Tokyo (JP)

(72) Inventors: Toshiro Umezaki, Fukuoka (JP); Tomoyuki Hasegawa, Yamagata (JP); Masatoshi Suda, Yamagata (JP)

(73) Assignees: Toshiro Umezaki, Fukuoka (JP); KOKEN CO., LTD., Tokyo (JP)

( * ) Notice: Subject to any disclaimer, the term of this patent is extended or adjusted under 35 U.S.C. 154(b) by 259 days.

(21) Appl. No.: 16/346,121

(22) PCT Filed: Nov. 7, 2017

(86) PCT No.: PCT/JP2017/040056
§ 371 (c)(1),
(2) Date: Apr. 30, 2019

(87) PCT Pub. No.: WO2018/088385
PCT Pub. Date: May 17, 2018

(65) Prior Publication Data
US 2019/0262564 A1 Aug. 29, 2019

(30) Foreign Application Priority Data
Nov. 8, 2016 (JP) .............................. JP2016-218317

(51) Int. Cl.
*A61M 16/04* (2006.01)

(52) U.S. Cl.
CPC ........ *A61M 16/0475* (2014.02); *A61M 16/04* (2013.01); *A61M 16/0468* (2013.01)

(58) Field of Classification Search
None
See application file for complete search history.

(56) References Cited

U.S. PATENT DOCUMENTS 4,037,605 A 7/1977 Firth
4,280,492 A * 7/1981 Latham
(Continued)

FOREIGN PATENT DOCUMENTS

JP 2006130015 A 5/2006
JP 2007050020 A 3/2007
(Continued)

OTHER PUBLICATIONS

International Search Report and Written Opinion issued in corresponding International Patent Application No. PCT/JP20171040056 (with English translation of International Search Report) dated Dec. 12, 2017 (7 pages).

(Continued)

*Primary Examiner* — Rachel T Sippel
(74) *Attorney, Agent, or Firm* — Kilyk & Bowersox, P.L.L.C.

(57) ABSTRACT

Provided is a tracheostomy tube having a freely openable/closable fenestration without substantially narrowing an inner cavity of the tracheostomy tube. It has been found that each of two tracheostomy tubes having the configurations (A) and (B) has the fenestration that is freely openable/closable with use of a shutter without substantially narrowing the inner cavity of the tracheostomy tube.

3 Claims, 3 Drawing Sheets

(56) References Cited

U.S. PATENT DOCUMENTS

| | | | | |
|---|---|---|---|---|
| 5,056,515 | A | * | 10/1991 | Abel |
| 5,771,888 | A | * | 6/1998 | Keim |
| 2007/0144526 | A1 | * | 6/2007 | Blom |
| 2009/0095302 | A1 | | 4/2009 | Blom |

FOREIGN PATENT DOCUMENTS

| | | | |
|---|---|---|---|
| JP | 2016026542 A | | 2/2016 |
| WO | 2016038323 A1 | | 3/2016 |
| WO | WO-2016038323 A1 | * | 3/2016 |

OTHER PUBLICATIONS

Extended European Search Report issued in corresponding European Patent Application No. 178702395 dated May 19, 2020 (6 pages).

* cited by examiner

FIG. 1A
FIG. 1B
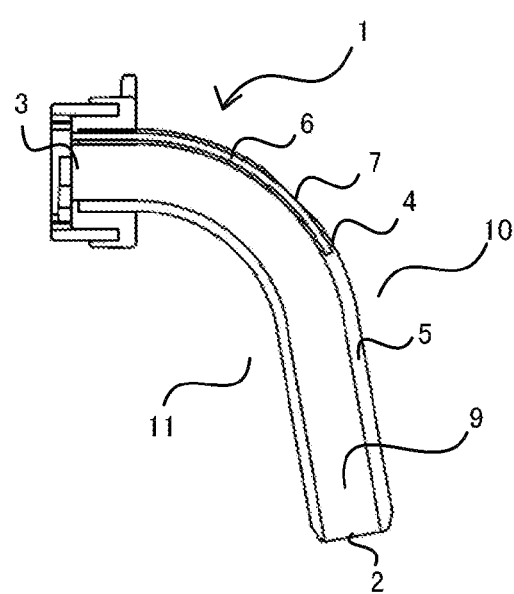
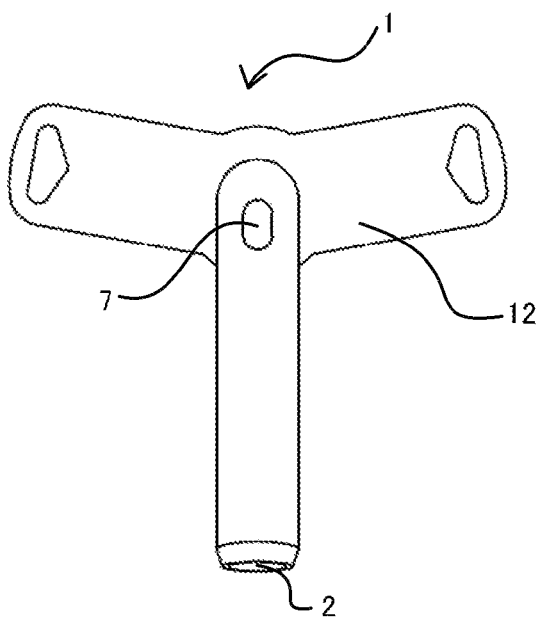
FIG. 2A
FIG. 2B
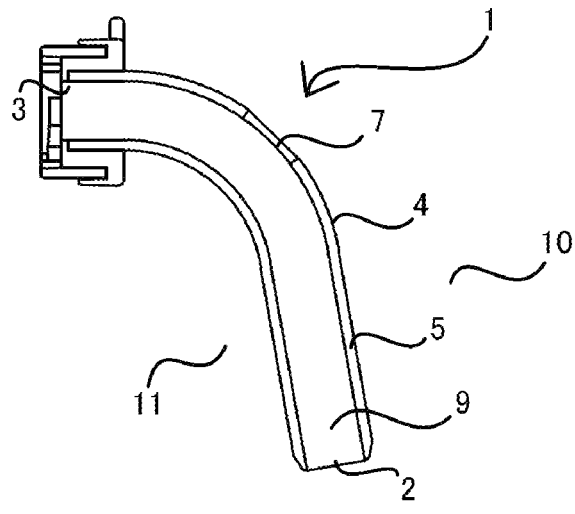
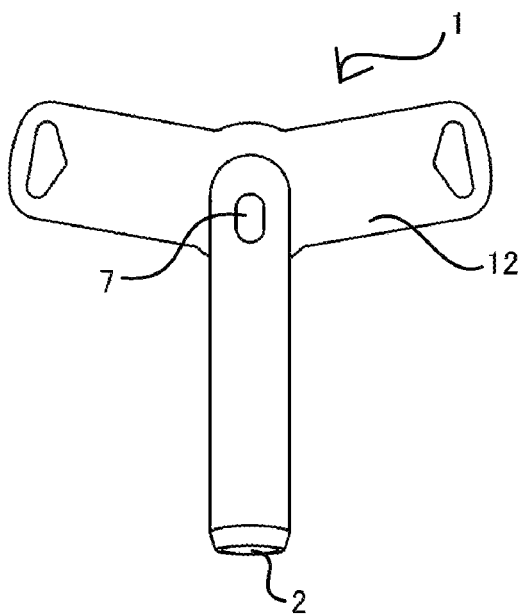

TRACHEOTOMY TUBE HAVING FREELY OPENABLE/CLOSABLE LATERAL HOLE

TECHNICAL FIELD

The present invention relates to a tracheostomy tube having a freely openable/closable fenestration, and more particularly, to a tracheostomy tube having a feely openable/closable fenestration for phonation and a tracheostomy tube set including the tracheostomy tube.

The present application is a National Stage Application of PCT/JP2017/040056, filed Nov. 7, 2017, which claims priority from Japanese Patent Application No. 2016-218317, which is incorporated herein by reference.

BACKGROUND ART (Related-Art Tracheostomy Tube Having Fenestration)

For a patient having some kind of stenosis in the upper airway (such as the nasal cavity, the oral cavity, and the glottis) or a patient who requires frequent suction of sputum in the trachea, a tracheal opening is surgically formed in the anterior neck region so that a tracheostomy tube is inserted into the trachea from the tracheal opening and placed therein.

The patient who has undergone a tracheostomy and has the tracheostomy tube placed therein respires from the anterior neck region through the tracheostomy tube without via the upper airway, and hence cannot produce phonation. However, the patient who is not able to produce the phonation is forced to be significantly inconvenienced. Thus, there exists the tracheostomy tube which has been devised to enable the phonation. For example, a tracheostomy tube having a fenestration formed on aback surface side of a tube part is sometimes used to cause expired air to pass through the upper airway. Further, a speech valve for allowing the expired air to more reliably pass through the upper airway is sometimes connected to a proximal end of the tracheostomy tube. With the speech valve, a full amount of expired air passes through the fenestration into the upper airway without leaking from the proximal end of the tracheostomy tube. Hence, clear sounds can more easily be produced (see Non Patent Literature 1).

The fenestration is necessary for phonation. Meanwhile, when a suction tube is inserted from an inner cavity of the tracheostomy tube into the trachea, there are the following risks. For example, a distal end of the suction tube may project from the fenestration. Accidentally aspired sputum may flow into the inner cavity of the tracheostomy tube from the fenestration to reach the lungs to be likely to cause aspiration pneumonia. A granulation tissue may penetrate into the fenestration to prevent the tracheostomy tube from being removed therefrom.

Specifically, the fenestration is required at the time of phonation. However, the fenestration is not otherwise required.

As a method of solving the problem described above, there exists the tracheostomy tube using a system of closing the fenestration with insertion of a dedicated inner cylinder into the inner cavity of the tracheostomy tube and opening the fenestration with removal of the inner cylinder. With the above-mentioned method, however, when the inner cylinder is inserted, the inner cavity of the tracheostomy tube is narrowed correspondingly. Thus, the above-mention method has a disadvantage in difficulty of use for a patient having a weak ventilation function (see Non Patent Literature 1).

CITATION LIST

Non Patent Literature

[NPL 1] "Types of Tracheal Cannulas and Proper Uses thereof," the eighth edition (August 2014).

SUMMARY OF INVENTION

Technical Problem

An object of the present invention is to provide a tracheostomy tube having a freely openable/closable fenestration without substantially narrowing an inner cavity of the tracheostomy tube.

Solution to Problem

In order to achieve the object described above, the inventors of the present invention have verified that each of two tracheostomy tubes having the following configurations (A) and (B) has the fenestration that is freely openable/closable with use of a shutter without substantially narrowing the inner cavity of the tracheostomy tube and have achieved the present invention.

The tracheostomy tube has the following configuration:

(A) A tracheostomy tube having a distal end, a proximal end, and a curve-shaped portion, including: a fenestration formed through a wall of the tracheostomy tube, through which an inner cavity of the tracheostomy tube communicates with an outside; a shutter lumen formed in the wall of the tracheostomy tube, the shutter lumen being configured to extend from the proximal end of the tracheostomy tube in a direction toward the distal end along the curve-shaped portion of the tracheostomy tube, and to cross the fenestration; and a shutter to be removed from and inserted into the shutter lumen so as to freely open and close the fenestration.

The tracheostomy tube has the following configuration:

(B) A tracheostomy tube having a distal end, a proximal end, and a curve-shaped portion, including: a fenestration formed through a wall of the tracheostomy tube, through which an inner cavity of the tracheostomy tube communicates with an outside; and a shutter to be removed from and inserted into the inner cavity so as to freely open and close the fenestration.

That is, the present invention includes the following.

1. A tracheostomy tube having a distal end, a proximal end, and a curve-shaped portion, including: a fenestration formed through a wall of the tracheostomy tube, through which an inner cavity of the tracheostomy tube communicates with an outside; a shutter lumen formed in the wall of the tracheostomy tube, the shutter lumen being configured to extend from the proximal end of the tracheostomy tube in a direction toward the distal end along the curve-shaped portion of the tracheostomy tube, and to cross the fenestration; and a shutter to be removed from and inserted into the shutter lumen so as to freely open and close the fenestration, or a tracheostomy tube having a distal end, a proximal end, and a curve-shaped portion, including: a fenestration formed through a wall of the tracheostomy tube, through which an inner cavity of the tracheostomy tube communicates with an outside; and a shutter to be removed from and inserted into the inner cavity so as to freely open and close the fenestration.

2. A tracheostomy tube set, including:
(1) the tracheostomy tube of above-mentioned Item 1; and
(2) a connector with shutter.
3. The tracheostomy tube set according to claim 2, further including a one-way valve, wherein the tracheostomy tube set is a speech tracheostomy tube set.

Advantageous Effects of Invention

The tracheostomy tube and the tracheostomy tube set including the tracheostomy tube according to the present invention have the following effects without substantially narrowing the inner cavity of the tracheostomy tube.
(1) Phonation is enabled by opening the fenestration.
(2) A suction tube can be correctly inserted without projecting from the fenestration by closing the fenestration.
(3) Penetration of a granulation tissue into the fenestration can be prevented by closing the fenestration.
(4) Insufflation from a mechanical ventilator can be prevented from leaking into the upper airway by closing the fenestration at the time of connection to the mechanical ventilator.
(5) In a cuffed tracheostomy tube, by closing the fenestration, accidentally aspired sputum can be prevented from flowing from the fenestration into the inner cavity of the tracheostomy tube and reaching the lungs.
(6) In contrast to the related-art tracheostomy tube, the tracheostomy tube of the present invention does not use an inner cylinder. Thus, there is no risk of scraping off secretion accumulated inside an outer cylinder into the trachea, which may occur when the inner cylinder is to be remounted.

BRIEF DESCRIPTION OF DRAWINGS

FIG. 1A is an overall sectional view (side view) of a tracheostomy tube (A),
and FIG. 1B is a back view of a tracheostomy tube set including the tracheostomy tube (A).
FIG. 2A is an overall sectional view (side view) of a tracheostomy tube (B),
and FIG. 2B is a back view of a tracheostomy tube set including the tracheostomy tube (B).

Figure 3A:
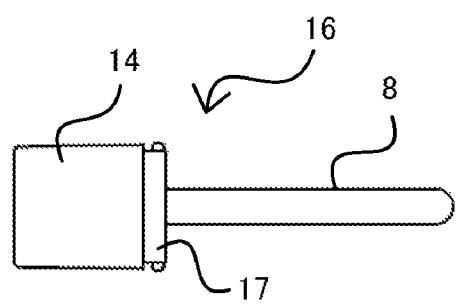
FIG. 3A is a top view of a connector with shutter (16)

DESCRIPTION OF EMBODIMENT (Subject Matter of the Present Invention)
Hereinafter, a mode for carrying out the present invention is described. However, the mode is not limitative of the scope of the claims. A tracheostomy tube of the present invention has a tracheostomy tube configuration (A) or a tracheostomy tube configuration (B) described below.
A tracheostomy tube 1 having the following configuration (A).
The tracheostomy tube 1 having a distal end 2, a proximal end 3, and a curved-shaped portion 4 includes:
a fenestration 7 formed through a wall 5 of the tracheostomy tube, through which an inner cavity 9 of the tracheostomy tube communicates with an outside;
a shutter lumen 6 formed in the wall 5 of the tracheostomy tube to extend from the proximal end 3 of the tracheostomy tube 1 in a direction toward the distal end 2 along the curve-shaped portion 4 of the tracheostomy tube 1 and cross the fenestration 7; and
a shutter 8 to be removed from and inserted into the shutter lumen 6 so as to freely open and close the fenestration 7.
The tracheostomy tube 1 having the following configuration (B).
The tracheostomy tube 1 having the distal end 2, the proximal end 3, and the curve-shaped portion 4 includes:
the fenestration 7 formed through the wall 5 of the tracheostomy tube, through which the inner cavity 9 of the tracheostomy tube communicates with the outside; and
the shutter 8 to be removed from and inserted into the inner cavity 9 so as to freely open and close the fenestration 7.

[Tracheostomy Tube (A)]
The tracheostomy tube (A) of the present invention has, as illustrated in FIG. 1A, the distal end 2, the proximal end 3, and the curved-shape portion 4. The fenestration 7 is formed through the wall 5 on a back surface 10 side of the tracheostomy tube (A). The inner cavity 9 of the tracheostomy tube communicates with an outside (outer side of the tracheostomy tube 1) through the fenestration 7. A position of the fenestration 7 is not particularly limited. However, it is preferred that the fenestration 7 be formed in the curved-shape portion 4 or the vicinity thereof. The shutter lumen 6 is formed in the wall 5 of the tracheostomy tube (A) on the back surface 10 side. The shutter lumen 6 is formed to extend from the proximal end 3 of the tracheostomy tube 1 in a direction toward the distal end 2 along the curve-shaped portion 4 of the tracheostomy tube 1, and to cross (cross substantially orthogonally to) the fenestration 7. A distal end of the shutter lumen 6 does not pass through the wall 5 of the tracheostomy tube. Note that, the presence of the fenestration 7 allows expired air to pass through the upper airway.
As a material of the tracheostomy tube 1, for example, polyvinyl chloride, polyurethane, or a silicone rubber is used as in the case of a tracheostomy tube publicly known by itself.
A shape of the fenestration 7 is not particularly limited, and a circle, an ellipsoid, a rectangle, and a rounded rectangle may be exemplified. A width of the fenestration 7 depends on a diameter of the tracheostomy tube 1 and falls within a range of from approximately 1 mm to 10 mm. The number of the fenestration 7 is not necessarily one. The fenestration 7 may be divided into a plurality of parts.
The shutter lumen 6 is not particularly limited as long as the shutter lumen 6 is formed in the wall 5 of the tracheostomy tube to extend from the proximal end 3 side, and to cross the fenestration 7 so as to form a cavity. For example, a hole having a rectangular cross section may be exemplified. A width of the shutter lumen 6 is at least equal to or larger than the width of the fenestration 7. It is preferred that, for example, the width of the shutter lumen 6 be larger than the width of the fenestration 7 by 1 mm to 3 mm to allow the shutter 8 to pass therethrough.

[Tracheostomy Tube (B)]
The tracheostomy tube (B) of the present invention has, as illustrated in FIG. 2A, the distal end 2, the proximal end 3, and the curved-shape portion 4. The fenestration 7 is formed through the wall 5 on a back surface 10 side of the tracheostomy tube (B). The inner cavity 9 of the tracheostomy tube communicates with an outside through the fenestration 7. Note that, the presence of the fenestration 7 allows expired air to pass through the upper airway. The position of the fenestration 7 is not particularly limited. However, it is preferred that the fenestration 7 be formed in the vicinity of the curve-shaped portion 4.

(Shutter 8)

A shape, a width, and a thickness of the shutter 8 to be inserted into and removed from the tracheostomy tube (A) are not particularly limited as long as the shutter 8 can be inserted into and removed from the shutter lumen 6 so as to open and close the fenestration 7.

A shape, a width, and a thickness of the shutter 8 to be inserted into and removed from the tracheostomy tube (B) are not particularly limited as long as the shutter 8 can be inserted into and removed from the inner cavity 9 of the tracheostomy tube so as to open and close the fenestration 7.

For example, the shutter 8 has a rectangular plate-like shape having elasticity and may be curved in accordance with the curve-shaped portion 4 of the tracheostomy tube 1. The distal end (distal end 2 side) of the shutter 8 may be chamfered or rounded so as to easily be inserted into the shutter lumen 6.

A material of the shutter 8 is not particularly limited. For example, polypropylene, polyethylene, polycarbonate, a fluorine resin, nylon, polyarylate, polyvinyl chloride, polyurethane, and other plastics and metals may be used.

(Connector with Shutter 16)

Figure 3B:
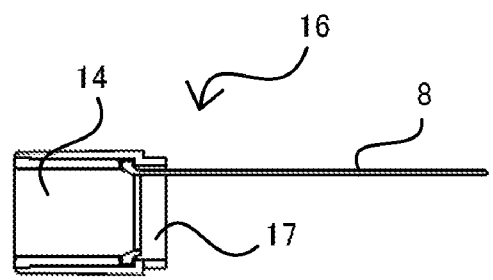
FIG. 3B is a sectional view (side view) of the connector with shutter (16).

A connector with shutter 16 includes at least the shutter 8 and a connector 14 (see FIGS. 3A and 3B). As the connector 14, a commercially available connector publicly known by itself (see Non Patent Literature 1) may be adopted. The connector with shutter 16 may further include a tracheostomy tube fixing portion 17 for the connector with shutter.

The tracheostomy tube fixing portion 17 for the connector with shutter may have a joining, fitting, coupling, locking, or threading (male thread, female thread) relationship with a valve and connector fixing portion 15 of the tracheostomy tube 1 so as to prevent accidental drop-off of the shutter 8 or removal from the tracheostomy tube 1.

(Valve 13)

As the valve 13, a commercially available valve publicly known by itself (see Non Patent Literature 1) may be adopted. The tracheostomy tube fixing portion 18 for the valve may have a joining, fitting, coupling, locking, or threading (male thread, female thread) relationship with a valve and connector fixing portion 15 of the tracheostomy tube 1 so as to prevent the removal from the tracheostomy tube 1.

The valve 13 may be used as a speech valve when a one-way valve is used. The one-way valve (speech valve) has such a structure of being opened at the time of inspiration and being closed at the time of expiration.

(Tracheostomy Tube Set)

A tracheostomy tube set includes at least the tracheostomy tube 1 and the connector with shutter 16, and further includes the following as needed.

A neck plate (frame) 12: The neck plate 12 may be provided in the vicinity of the proximal end 3 of the tracheostomy tube 1 so as to be orthogonal to an axis of the tube. A cord is caused to pass through holes formed at both ends of the neck plate 12 so as to be hung around the neck region. In this manner, the tracheostomy tube 1 placed in a tracheal opening can be fixed so as not to accidentally drop off.

A cuff: The cuff may be provided in the vicinity of the distal end 2 of the tracheostomy tube 1. The cuff is a balloon inflatable with air. Through inflation of the cuff, a gap between the trachea and the tracheostomy tube 1 can be closed. In this manner, when the tracheostomy tube 1 is connected to a mechanical ventilator, air blown from the mechanical ventilator can be prevented from leaking through the gap between the trachea and the tracheostomy tube 1 into the upper airway.

Note that, when the cuff is provided, an airway lumen configured to inflate the cuff is required to be formed in a portion of a wall of the tracheostomy tube 1 along an axial direction of the tube so as to allow passage of air from and to the outside.

A tube configured to inflate the cuff.

A suction tube: When the cuff is provided, the tube sucks, for example, sputum accumulated on the cuff.

(Speech Tracheostomy Tube Set)

The speech tracheostomy tube set includes at least the tracheostomy tube 1, the connector with shutter 16, and the valve 13 being the one-way valve.

(Mode of Use of Tracheostomy Tube 1)

Figure 4A:
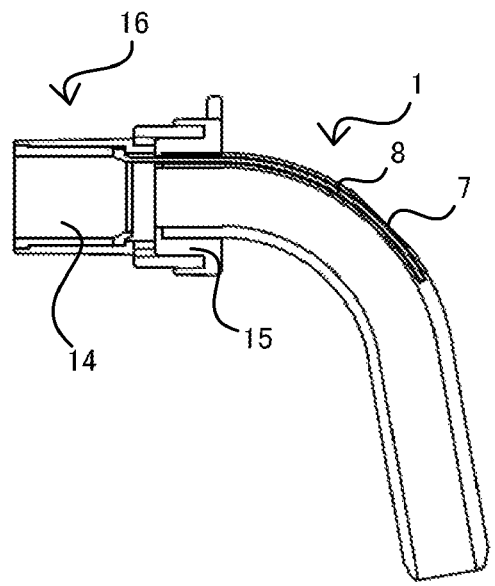
FIG. 4A is a view of the tracheostomy tube (A) in a state in which a fenestration (7) is closed with a shutter (8)
Figure 4B:
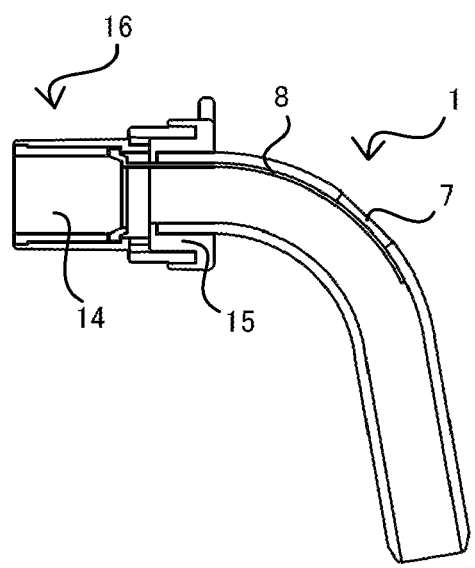
FIG. 4B is a view of the tracheostomy tube (B) in a state in which the fenestration (7) is closed with the shutter (8).

When the patient is not required to produce phonation, the shutter 8 is inserted into the shutter lumen 6 to close the fenestration 7 [FIG. 4A, FIG. 4B]. With the closure of the fenestration 7, the suction tube can be correctly inserted without projecting from the fenestration 7 so as to prevent a granulation tissue from penetrating into the fenestration 7. Further, when the phonation is not required, the mechanical ventilator or an artificial nose (humidification filter) is sometimes connected, and thus can be connected via the connector 14 (for example, designed in accordance with the JIS standard) of the connector with shutter 16. When the mechanical ventilator is to be connected to the tracheostomy tube 1, the shutter 8 is inserted into the shutter lumen 6 to close the fenestration 7. In this manner, leakage of air into the upper airway can be prevented.

Figure 5A:
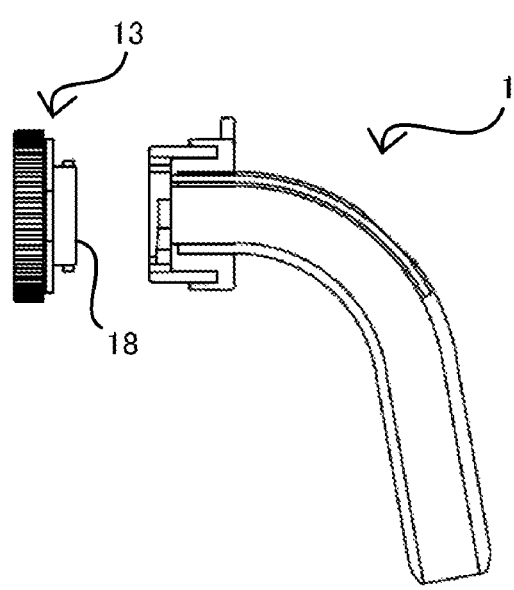
FIG. 5A is a view of the tracheostomy tube (A) before connection of a valve (13)
Figure 5B:
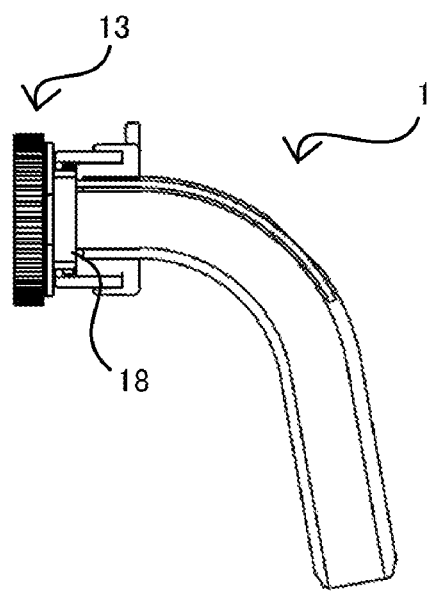
FIG. 5B is a view of the tracheostomy tube (A) after the connection of the valve (13).

When the patient is required to produce the phonation, the shutter 8 is removed from the shutter lumen. Instead, the valve 13 being the one-way valve is connected (mounted) to the tracheostomy tube 1 [FIG. 5A, FIG. 5B].

INDUSTRIAL APPLICABILITY

There can be provided the tracheostomy tube having the freely openable/closable fenestration without substantially narrowing the inner cavity of the tracheostomy tube.

REFERENCE SIGNS LIST 1. tracheostomy tube
2. distal end
3. proximal end
4. curve-shaped portion
5. wall of tracheostomy tube
6. shutter lumen
7. fenestration
8. shutter
9. inner cavity of the tracheostomy tube
10. back surface (back surface side)
11. intrados side
12. neck plate
13. valve
14. connector
15. valve and connector fixing portion
16. connector with shutter
17. tracheostomy tube fixing portion for connector with shutter
18. tracheostomy tube fixing portion for valve

The invention claimed is:

1. A tracheostomy tube having a distal end, a proximal end, and a curve-shaped portion, comprising:
    a fenestration formed through a wall of the tracheostomy tube, through which an inner cavity of the tracheostomy tube communicates with an outside;
    a shutter lumen formed in the wall of the tracheostomy tube, the shutter lumen being configured to extend from the proximal end of the tracheostomy tube in a direction toward the distal end along the curve-shaped portion of the tracheostomy tube, and to cross the fenestration; and
    a shutter to be removed from and inserted into the shutter lumen so as to freely open and close the fenestration such that the fenestration is unable to be freely open while the shutter is fully inserted into the shutter lumen.

2. A tracheostomy tube set, comprising:
    (1) the tracheostomy tube of claim 1; and
    (2) a connector with the shutter.

3. The tracheostomy tube set according to claim 2, further comprising a one-way valve, wherein the tracheostomy tube set is a speech tracheostomy tube set.

* * * * *